United States Patent [19]

Gotou et al.

[11] Patent Number: 4,601,577
[45] Date of Patent: Jul. 22, 1986

[54] METHOD AND APPARATUS FOR DETECTING DEFECTS IN A PATTERN

[75] Inventors: Yukihiro Gotou; Etsuji Suzuki, both of Yokohama, Japan

[73] Assignee: Tokyo Shibaura Denki Kabushiki Kaisha, Kawasaki, Japan

[21] Appl. No.: 534,119

[22] Filed: Sep. 20, 1983

[30] Foreign Application Priority Data

Sep. 21, 1982 [JP] Japan .................. 57-163204
Oct. 27, 1982 [JP] Japan .................. 57-187470
Jan. 24, 1983 [JP] Japan .................. 58-9662

[51] Int. Cl.⁴ .................................. G01N 21/47
[52] U.S. Cl. .................................. 356/237
[58] Field of Search ........... 356/237, 310, 337, 340, 356/121; 350/271, 275, 236, 524, 525

[56] References Cited

U.S. PATENT DOCUMENTS 3,186,296  6/1965  Erban ....................... 356/237
3,658,420  4/1972  Axelrod .................... 356/237
4,297,032  10/1981 Temple ..................... 356/337

Primary Examiner—John E. Kittle
Assistant Examiner—Thomas C. Saitta
Attorney, Agent, or Firm—Cushman, Darby and Cushman

[57] ABSTRACT

A method and apparatus for detecting defects in a pattern are disclosed. The defect detecting method is comprised of a step of dark-field illuminating a patterned object with a directionality and a step for detecting only the defect component by erasing the pattern component in a pattern image formed by the dark-field illumination. The apparatus comprises an illuminating device for dark-field illuminating a patterned object with parallel rays, an image pick-up device for picking up a pattern image, which is disposed just above the pattern, and a data processing circuit for processing the picked up image signal to detect a defect.

17 Claims, 21 Drawing Figures

F I G. 15
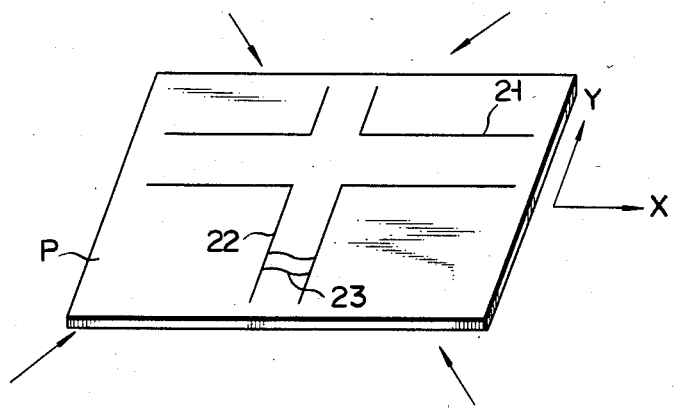
F I G. 16
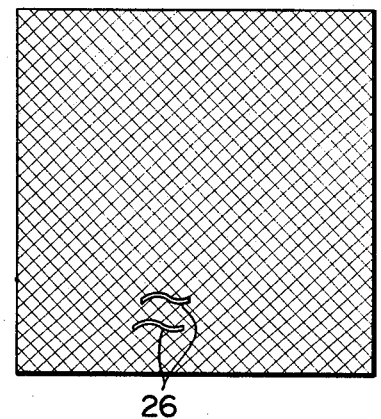

METHOD AND APPARATUS FOR DETECTING DEFECTS IN A PATTERN

BACKGROUND OF THE INVENTION

The present invention relates to a method and apparatus for detecting defects in a pattern having directionality as a pattern formed on a semiconductor pellet, for example.

The manufacturing process of semiconductor devices includes several steps of: for example, forming a plurality of semiconductor regions by injecting impurities into a semiconductor wafer, forming an oxide film and an electrode layer on the semiconductor wafer, dividing the semiconductor wafer into a plurality of chips, and applying the wire bonding to the separated chips. As is well known, the manufacturing process of a semiconductor device is a typical example of the fine work requiring complicated and sophisticated technique to manufacture. When a defect is found in the pattern during the course of the manufacturing process, it is desirable, therefore, to pick up and remove such defective semiproduct before the process reaches the final step.

Many approaches to inspect defects in a pattern formed on the semiconductor wafer surface have been proposed. In one of such proposals the configurations of the corresponding portions in the two adjacent chips on a semiconductor wafer are successively compared. When an inconsistency is found in the results of the successive comparisons, it is determined to be a defect. Before the wafer is divided into a number of individual chips, this approach can secure a highly accurate detection because the relative positions of the chips are fixed, and the corresponding portions to be compared can easily and correctly be specified. It is evident, however, that defect detection cannot be carried out in the steps following the wafer dividing step, for example, in the dicing step for obtaining individual chips and the step for picking up these individual chips. For this reason, the approach under discussion requires another defect detection step after chip separation. The additional defect detection step, however, encounters a difficulty in specifying the corresponding portions on the adjacent chips to be compared, since those individual chips are separated. This difficulty in specifying the corresponding portions on the chips leads to inaccurances in the detection.

SUMMARY OF THE INVENTION

Accordingly, an object of the present invention is to provide a method and an apparatus for accurately detecting defects in a pattern on a chip even after the chip has been separated.

According to the invention, there is provided a method of detecting defects in a pattern comprising the steps of dark-field illuminating a patterned object with a directionality by substantially parallel rays, and detecting only a defect component from a pattern image formed by the dark-field illumination.

There is further provided a defect detecting apparatus comprising means for dark-field illuminating a patterned object with substantially parallel rays of light, means disposed just above said pattern for detecting a pattern image signal by picking up a pattern image and converting the pattern image into electrical signals, and means for processing the pattern image signal from said pattern image signal detecting means.

BRIEF DESCRIPTION OF THE DRAWINGS

FIG. 15 shows a pattern to be inspected and having a defect; and

FIG. 16 shows an image formed by the apparatus of FIG. 13.

DETAILED DESCRIPTION OF THE PREFERRED EMBODIMENTS

Figure 1:
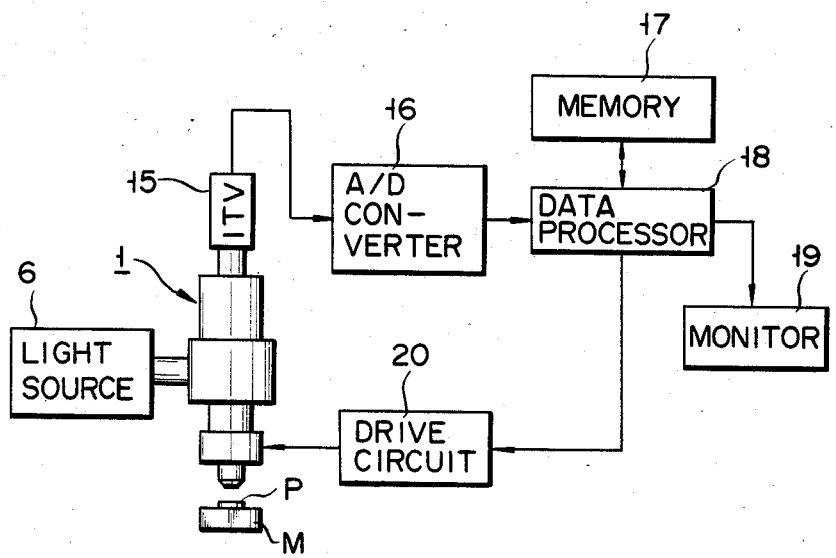
FIG. 1 is a view illustrating a defect detecting apparatus according to the present invention.
Figure 2:
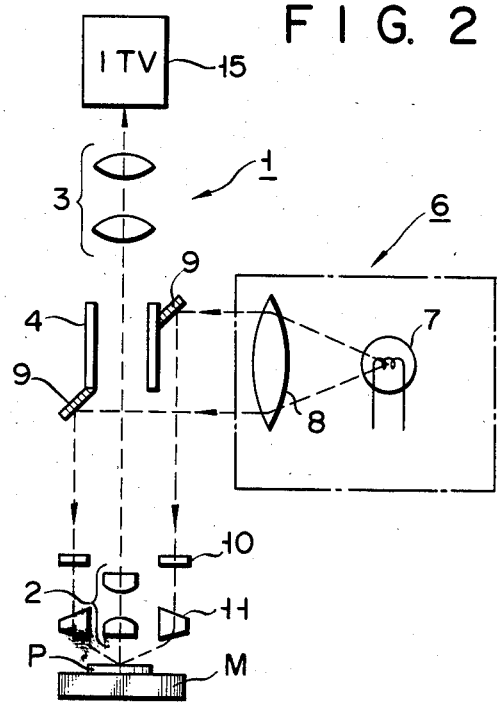
FIG. 2 shows a schematic diagram of an optical system used in the defect detecting apparatus of FIG. 1.

Reference is first made to FIGS. 1 and 2. A microscope 1 is disposed right above a pattern P on the surface of an object M under inspection. The microscope 1 is also coupled with an industrial television (ITV) 15 as an image pick-up device. The output of the ITV 15 is connected to an A/D (analog to digital) converter 16 the output of which is connected to a data processor 18. The data processor 18 is connected to a memory 17. The output of the data processor 18 is connected to a monitor 19. A drive circuit 20, connected to the data processor 18, is controlled by a control signal from the data processor 18. As shown in FIG. 2, a light source 6 includes a lamp 7 and a convex lens 8 for collimating the rays of light from the lamp 7. The microscope 1 includes an objective system 2 disposed adjacent to the object M under inspection, an ocular system 3 disposed facing the ITV 15, a reflecting mirror 9 which is mounted to a mirror tube 4 and directs the parallel rays of light emanating from the light source 6 toward the object M under inspection, a slit plate 10 which is installed in the optical path of the reflecting light from the reflecting mirror 9 and rotated by a drive circuit 20 including a pulse motor, for example, and a ring-like condensing lens system 11 for dark-field illumination and which is disposed arrounding the objective system 2 and receives the rays passed through a pair of slits of the slit plate 10 (FIG. 4) to condense them on the pattern P on the object M under inspection.

Figure 3:
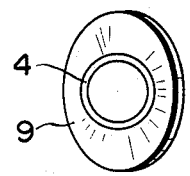
FIG. 3 is a plan view of a mirror assembly having a mirror tube and a reflecting mirror.
Figure 4:
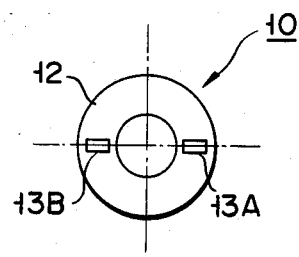
FIG. 4 is a plan view of a slit plate.

The reflecting mirror 9 is a collar-like member set at an angle around the mirror tube 4, as shown in FIG. 3. The slit plate 10 is a ring-like plate member 12, as shown in FIG. 4. The slit plate 10 has a pair of slits 13A and 13B which are disposed symmetrically with respect to a center of the slit plate 10.

The light source 6 emits parallel rays of light for illuminating the object M under inspection. The ITV 15 picks up the pattern P magnified by the microscope 1 and converts the rays representing the pattern into corresponding electrical signals. The A/D converter 16 converts the pattern image signals from the ITV 15 into digital signals. The memory 17 stores the output signal from the A/D converter 16. The data processor 18 arithmetically processes the output signal from the memory 17 and the signal subsequently produced from the A/D converter 16 to check whether the pattern has a defect or not. The data processor 18 also controls the drive circuit 20 to rotate the slit plate 10. The monitor 19 displays a defect pattern image on the basis of a signal representing the presence of the defect pattern from the data processor 18. The drive circuit 20 responds to the control signal from the data processor 18 to operate and rotate the slit plate 10 at a predetermined angle.

The detection of a defect in the pattern by using the defect detection apparatus shown in FIGS. 1 and 2 will be described.

Figure 5:
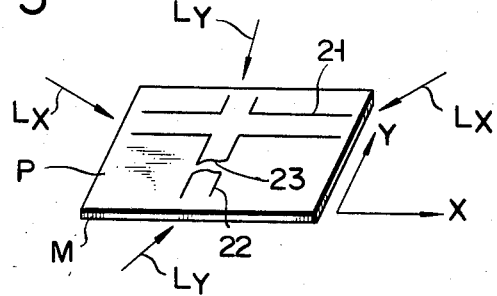
FIG. 5 shows an example of a pattern having a defect.

Generally, electrode layers 21 and 23 extending in the X- and Y-directions, which are displaced orthogonal to each other, are formed on the surface of the object M under inspection as a semiconductor chip for integrated circuits, for example, as shown in FIG. 5. Accordingly, a pattern having elongated projections extending in the X- and Y-directions and depressions arrayed in the same directions and defined by the elongations is formed on the surface of the chip M. In the example illustrated in FIG. 5, a disconnected portion, or defect portion denoted as 23, lies in the electrode layer 22.

To inspect this defect portion, the object M under inspection is set just below the objective system 2 of the microscope shown in FIGS. 1 and 2. The direction of a straight line connecting the pair of slits 13A and 13B formed on the slit plate 10 is set so as to coincide with the Y-direction of the pattern P, i.e. the direction of the elongation of the electrode layer 22. Under this condition, the light source 6 radiates the parallel rays onto the reflecting mirror 9 of the microscope 1. The reflecting mirror 9 deflects the incident parallel rays toward the object M under inspection. Arranged in the optical path of the deflected rays of light are the slit plate 10 and the condensing lens system 11 for dark-field illumination. The rays hit the slit plate 10 and pass in part through the pair of slits 13A and 13B thereof, and are incident on the condensing lens system 11. The rays then are condensed on the pattern P by means of the condensing lens system 11 and illuminate the pattern P. Since the Y-direction of the pattern P is aligned in the direction of the straight line connecting the pair of the slits 13A and 13B of the slit plate 10, as described above, the rays that passed through the slits 13A and 13B of the slit plate 10 are directed in the Y-direction of the pattern P. In other words, the pattern P is illuminated with the rays $L_Y$ not including the X-direction component of rays. Accordingly, a pattern image A1 (FIG. 6A) picked up by the ITV 15 through the microscope 1 contains only an image of the electrode layer 21 in the X-direction and an image 26 of the defect portion 23 with no image of the electrode layer 22 in the Y-direction. The defect image 26 has X- and Y-direction components because it has a sharp edge. The ITV 15 converts this pattern image into corresponding electrical signals. The converted electrical signal is input to the A/D converter 16 where the electrical signal is converted into a digital signal. The digital signal is then sent through the data processor 18 to the memory 17 where it is temporarily stored.

Figures 6A, 6B, 6C:
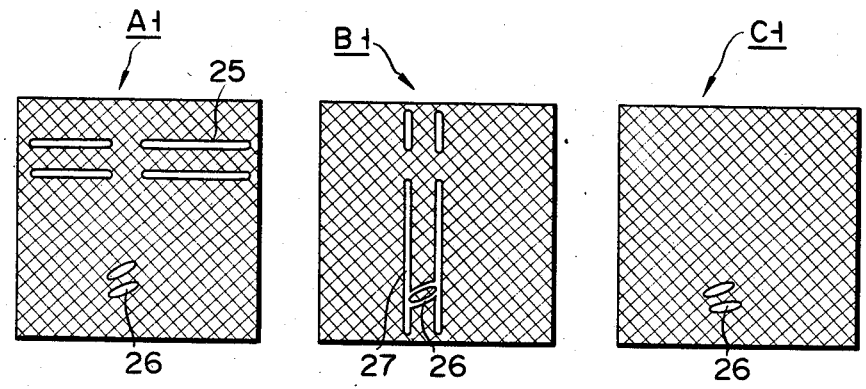
FIGS. 6A and 6B show respectively pattern images picked up by an image pick-up device using the slit shown in FIG. 4.
FIG. 6C shows an image as the logical product of the images of FIGS. 6A and 6B.

When the data of a pattern image A1 shown in FIG. 6A stored in the memory 17, the drive circuit 20 receives the count signal from the data processor 18 to rotate the slit 10 at an angle of about 90°. With the 90° rotation of the slit plate 10, the X-direction of the pattern P is coincident with the line connecting the slits 13A and 13B on the slit plate 10. Thus, this line is in the same direction as the extending direction of the electrode layer 21 of the pattern P. Under this condition, the rays passed through the slits 13A and 13B of the slit plate 10 illuminate the pattern P slantly from above in the X-direction of the pattern P. Thus, the pattern P is illuminated with the parallel rays $L_X$ having no Y-directional component. Thus, a pattern image B1 picked up at this time by the ITV 15 contains an image 27 of the electrode 22 extending in the Y-direction and an image 26 of the defect portion having sharp X- and Y-components, as illustrated in FIG. 6B. The image B1 is processed by the ITV 15 and the A/D converter 16 as the image A1 is done, and input to the data processor 18. The data processor 18 reads out the data of the corresponding picture elements in the image A1 stored in the memory 17 every time it receives the electrical signals of the corresponding picture elements in the image B1. Then, the data processor 18 forms the logical product of both signals. Therefore, when both the signals are logical "1" for each picture element pair, the data processor 18 produces logical "1". The logical product data is input to the monitor 19 where it is displayed as an image C1, as shown in FIG. 6C. As seen, the image C1 of the logical product of the images A1 and B1 contains only the image 26 of the defect portion 23 since the electrode images 25 and 27 are cancelled out.

The process to find the defect portion is as mentioned above.

As seen from the foregoing, the defect detecting apparatus visualizes only the defect portion with the removal of the pattern images. Therefore, the defect detection is performed at a high accuracy. Therefore, a difficulty in specifying the corresponding positions on the individual separated chips is eliminated, leading to easy and effective detection.

Figure 7:
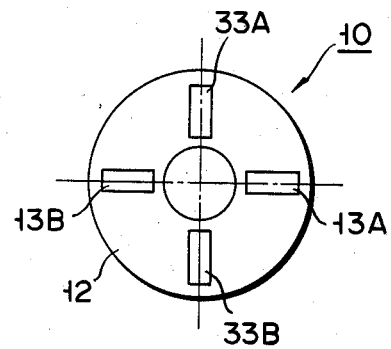
FIG. 7 shows a plan view of another example of the slit plate.

In FIG. 7, another example of the slit plate 10 is shown. This example is provided with two pairs of slits 13A, 13B, 33A and 33B each being disposed symmetrically with the center of the slit plate 10. Those pairs are disposed separated 90° from one another.

Figure 8:
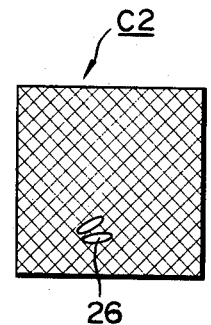
FIG. 8 shows a pattern image picked up by an image pick-up device using the slit plate of FIG. 7.

The following example has the slit plate 10 shown in FIG. 7 applied to the defect detecting apparatus shown in FIGS. 1 and 2. For defect detection, the slit plate 10 is set so that the straight lines connecting the pairs of the slits 13A, 13B, 33A and 33B are displaced by about 45° from the two crossed elongations of the pattern P as shown in FIG. 7. When the slit plate 10 is set at such an angle, the pattern P is illuminated at an angle from above and in a direction rotated by about 45° from the crossed straight lines in pattern P. Under this condition, the monitor 19 displays an image C2 containing only the image 26 of the defect portion 23 and not the images of the electrode layers 21 and 22, as shown in FIG. 8.

Figure 9:
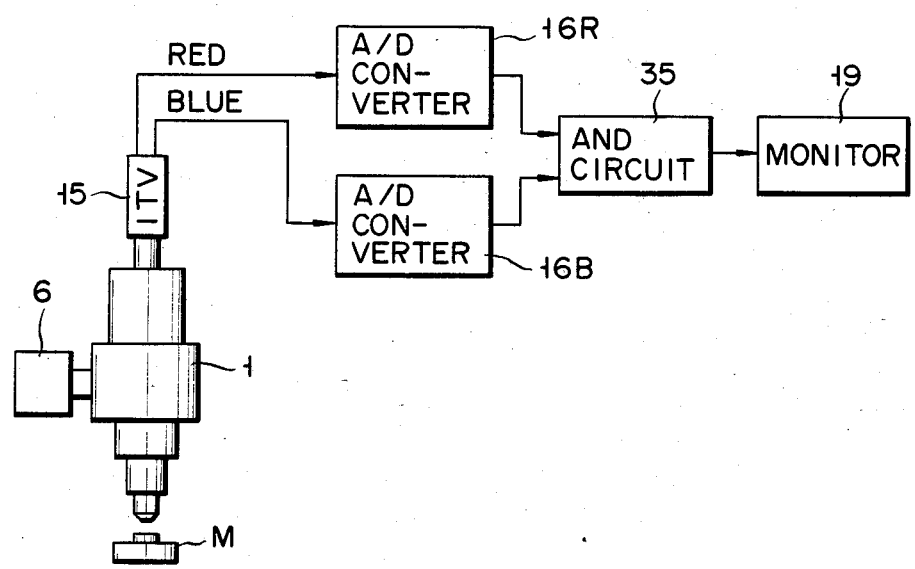
FIG. 9 is a block and schematic diagram illustrating another embodiment of a defect detecting apparatus according to the present invention.

A second embodiment of a defect detecting apparatus according to the present invention will be described referring to FIGS. 9 and 10.

The present embodiment is so designed that the pattern P is subjected to dark-field illumination with rays of different wavelengths, and pattern images formed by the light rays are taken out in a separate manner. For simplicity, like reference symbols are applied to like or equivalent portions in the embodiment of FIGS. 1 and 2. The arrangements of the microscope 1 and the light soruce 6 are the same as those of FIG. 2 and hence explanation thereof will be omitted.

Figure 10:
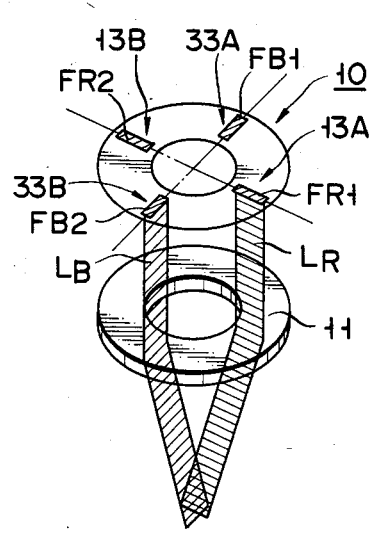
FIG. 10 shows a combination of a slit plate and a condensing lens used in the apparatus shown in FIG. 9.
Figure 11:
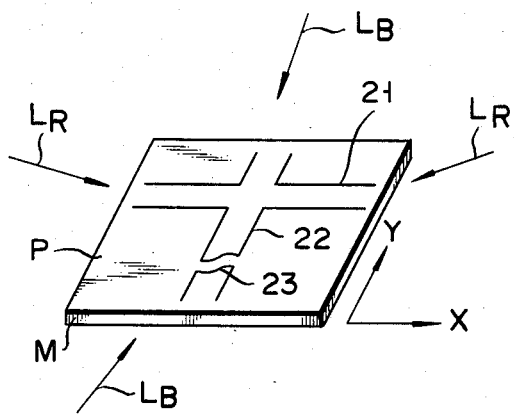
FIG. 11 shows a pattern to be subjected to the dark-field illumination.

Referring to FIG. 10, a slit plate 10 used in the present embodiment has two pairs of slits 13A, 13B, 33A and 33B. The slits of each pair are symmetrically disposed with respect to the center of the slit plate 10, and those slits are arranged about the center of the slit plate 10 displaced 90° apart. A condensing lens 11 is provided for condensing the rays passed through the slits 13A, 13B, 33A and 33B. The slits 13A and 13B are provided with red optical filters FR1 and FR2, respectively; the slits 33A and 33B with blue color filters FB1 and FB2, respectively. In the present embodiment, the ITV 15 is a color ITV. Further, this embodiment employs two A/D converters 16R and 16B for converting red and blue color image signals into digital signals. The digital signals from both A/D converters 16R and 16B are applied to an AND circuit 35 which logically multiplies both signals of every pair of the corresponding picture elements. The output signal from the AND circuit 35 is input to the monitor 19.

Figure 12A:
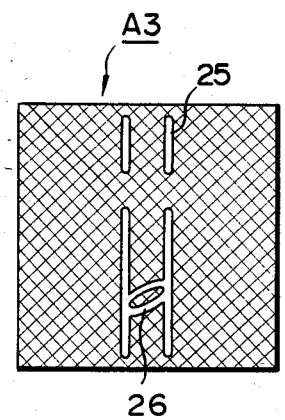
FIGS. 12A to 12C respectively show patterns formed by the apparatus of FIG. 9.
Figure 12B:
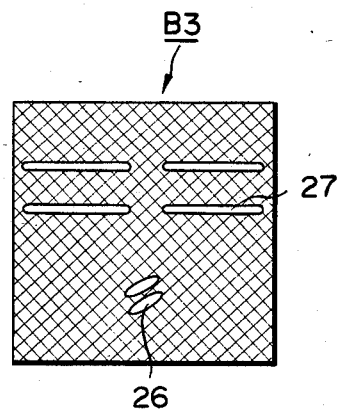
Figure 12C:
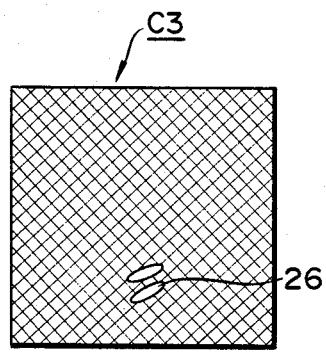

For detecting a defect in the pattern, the lines connecting the slit pairs are superposed on the crossed, elongated patterns in the pattern P, respectively. Under this condition, the red rays $L_R$ that pass through the red filters FR1 and FR2 provided in the slits 13A and 13B as parallel rays having no Y-directional component, illuminate the electrode layer 21 in the pattern P along its elongation at an angle from above. The blue rays $L_B$ that pass through the blue filters FB1 and FB2 provided in the slits 33A and 33B as the parallel rays, illuminate the pattern P at an angle from above and along the elongation of the electrode layer 22. The pattern P illuminated with the red and blue rays $L_R$ and $L_B$ is picked up as a red image A3 (FIG. 12A) and a blue image B3 (FIG. 12B). In this case, the red image A3 shown in FIG. 12A is formed by the red rays $L_R$ having no Y-directional component, and hence has an image 25 of the electrode layer 22 extending in the Y-direction, and an image 26 of the defect portion 23. Likewise, the blue image B3 shown in FIG. 12B is formed by the blue rays $L_B$, and therefore contains the image 27 of the electrode layer 21 extending in the X-direction and the image 26 of the defect portion 23. The color ITV 15 converts the red and blue images A3 and B3 into corresponding electrical signals. The red and blue electrical signals are applied to the A/D converters 16A and 16B where they are digitalized. The digital signals from the A/D converters 16R and 16B are input to the AND circuit 35. In turn, the AND circuit 35 logically multiplies the digital signals from the AND circuit 35 for each pair of the picture elements located at the corresponding positions in the adjacent chips. The logical product from the AND circuit 35 produces a logical "1" signal only when both the input signals are logical "1". The logical product signal is applied to the monitor 19. An image C3 displayed by the monitor 19 contains only the defect image 26, and not the images 25 and 27 of the electrode layers 21 and 22.

In this way, the defect 23 in the pattern P is detected.

Figure 13:
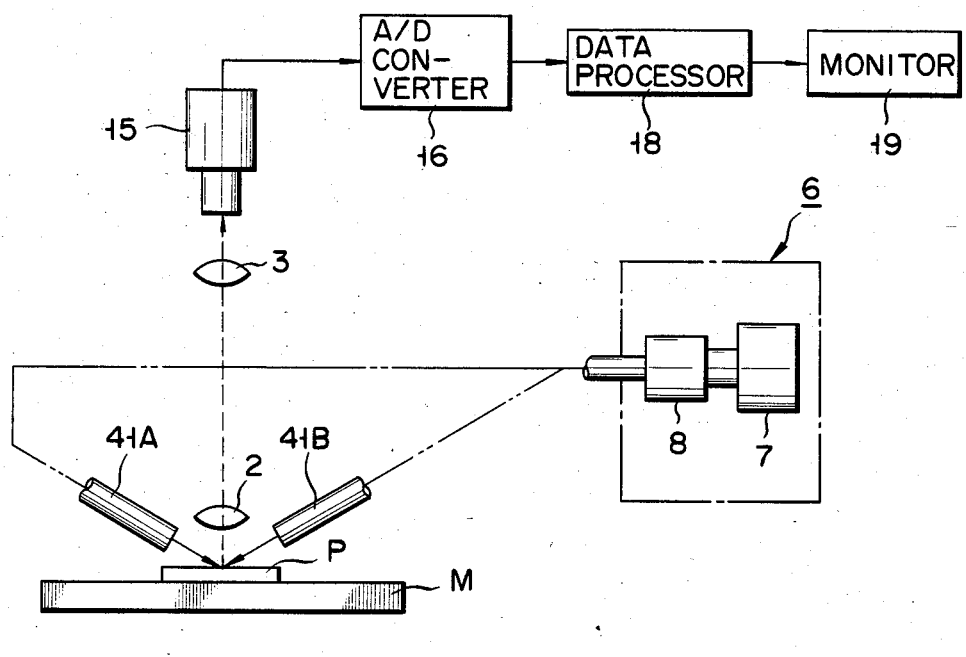
FIG. 13 shows a block and schematic diagram of yet another embodiment of a defect detecting apparatus according to the present invention.

Yet another embodiment of the defect detecting apparatus according to the present invention will be described referring to FIG. 13.

The present embodiment is so designed that the parallel rays emitted from the light source 6 are led through four optical fibers 41A–41D (fibers 41C and 41D being not shown in FIG. 13) the object M under inspection to dark-field illuminate the pattern P. In this embodiment, like or equivalent portions are designated by like reference symbols.

Figure 14A:
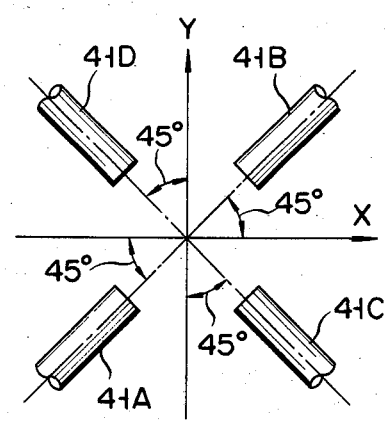
FIGS. 14A and 14B show respectively plan and side views of an arrangement of optical fibers used in the apparatus of FIG. 13.
Figure 14B:
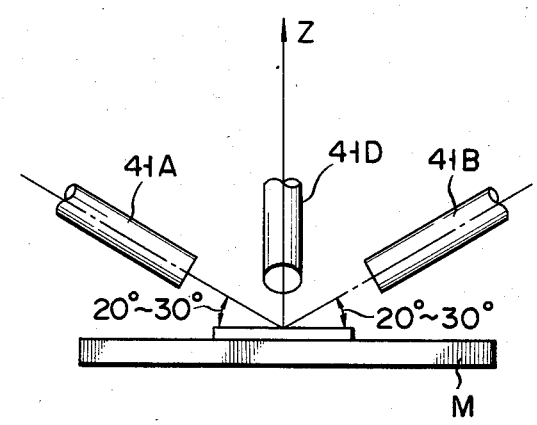

As shown in FIG. 14A, the optical axes of the optical fibers 41A–41D are displaced about 45° from the crossed elongations of the pattern P. Incidentally, FIG. 13 illustrates only two optical fibers 41A and 41B for ease of illustration.

In the present embodiment, the pattern P is simultaneously illuminated in a dark-field manner in four directions along the crossed elongations of the pattern P. In this case, the pattern P is illuminated in the four directions displaced by 45° from the crossed elongations of the pattern P. Therefore, there are no, or very few rays scattered vertically by the edges of the electrode layers 21 and 22. The pattern image picked up by the ITV 15 contains only the scattered rays reflected from the defect portion 23, as shown in FIG. 16. The image signal obtained by the ITV 15 is converted into a digital signal by the A/D converter 16 and input to the data processor 18. The signal processing is appropriately performed by the data processor 18 to obtain the size. Configuration and distribution of the defects, and then the signals containing the information are applied to the monitor 19. In turn, the monitor 19 visualizes the information obtained by the data processor 18.

It is preferable that the output terminals of the optical fibers 41A–41D have the optical axes raised by about 20° to about 30° from the plane of the pattern P. If the optical fibers 41A–41C are disposed at such an angle, the light rays reflected when the pattern P is slightly ragged or the chip bearing the pattern P is slanted, is reduced considerably compared with those when the optical fibers are disposed by a larger angle, for example, 50°–60°.

Further, with the angle set at 20°–30°, the problems caused when the angle of the optical fibers 41A–41D from the pattern P is less than 20° is eliminated. The problem is that scattering of light rays from the periphery of the defective part does not occur.

As was mentioned, the two crossed elongations of the pattern P are illuminated by the rays in four directions displaced by substantially 45° from those of the crossed elongations. This feature provides fairly high accuracy in the defect detection. Another feature of this embodiment is that the illumination system is composed of fine four optical fibers. Because of this feature, the end of the illumination system can be reduced in size. This feature is particularly advantageous when the pattern P must be illuminated at a small angle, for example, 20°–30°, of the illumination rays from the surface of the pattern P. The advantage resulting from the setting of the angle ranging from 20° to 30° between the incident illumination rays and the pattern P surface is correspondingly applicable for the embodiments of FIGS. 1, 2 and 9. As a matter of course, in this case, the illumination rays emanating from the condensing lens system 11 are applied to the pattern P at an angle in the range of 20°–30°.

While some specific embodiments of this invention have been described, this invention is not limited to such embodiments. For example, in the embodiments of FIGS. 1, 2 and 9, the slit plate 10 which is disposed in the optical path of the reflecting rays from the reflecting mirror 9, may be placed in the optical path of the rays incident on the reflecting mirror 9. The color ITV 15 in the FIG. 9 embodiment may be replaced by a monochrome ITV combined with appropriate color filters. The use of the color filters used in the FIG. 9 embodiment are preferable as the difference between the wavelengths of the colors is greater. It should be noted, however, that a case of a small wavelength difference is also involved in the present invention. For example, those colors may be red and green.

Further, in the slit-use embodiments, the displacement of the illuminating direction for the pattern P relative to the crossed elongations in the pattern P is not necessarily limited to 45°. This displacement may be of any angle if it can prevent the rays from being scattered from the pattern with directionality. Additionally, in the embodiment of FIG. 13, each illuminating direction has two illuminating sources. It is evident, however, that the use of the single illuminating source is also allowable. The function of the data processor 18 used in the FIGS. 1, 2 and 9 embodiment is expandable so as to be able to recognize the size, configuration, number, distribution, etc., of the defect in addition to the merely detecting the presence of a defect. Furthermore, the ITV 15 may be substituted by CCD phot array or other appropriate device.

It should be understood that the present invention is not limited by the above-mentioned embodiments, but may variously be changed and modified within the scope of the invention.

What is claimed is:

1. An apparatus for detecting a defect on a pattern having a portion extending in a first direction and a portion extending in a second direction orthogonal to said first direction comprising:
    means for dark field illuminating said pattern with first rays in said first direction and at a predetermined angle with respect to the surface of said pattern and dark field illuminating said pattern with second rays in said second directions and at said predetermined angle with respect to said surface of said pattern, said illuminating means comprising a light source for irradiating rays, a slit plate having a plurality of slits through which the rays of said light source pass, and a condensing lens for directing the rays having passed through said slits to said pattern at said predetermined angle so that they form said first and second rays;
    means for detecting a first image signal of said pattern when said pattern is illuminated with said first rays, and a second image signal of said pattern when said pattern is illuminated with said second rays; and
    means for logically multiplying said first and second image signals to provide an image of said defect.

2. An apparatus according to claim 1, wherein said slits comprise a pair of slits disposed in a single direction and symmetrically with respect to the center of said slit plate, and said slit plate is rotatable about said center so that said pair of slits can be aligned with said first and second directions such that, when said pair of slits are set to align with said first direction, the rays of said light source emitted through said pair of slits form said first rays, and when said pair of slits are set to align with said second direction, the rays of said light source emitted through said pair of slits form said second rays.

3. An apparatus according to claim 1, wherein said slits comprise a first pair of slits and a second pair of slits, said first pair of slits being disposed in a single direction and symmetrically with respect to the center of said slit plate, said second pair of slits being disposed in a direction orthogonal to said last recited direction and symmetrically with respect to the center of said slit plate, said first pair of slits being so set as to align with said first direction so that rays of said light source emitted through said first pair of slits form said first rays, and said second pair of slits being so set as to align with said second direction so that rays of said light source emitted through said second pair of slits form said second rays.

4. An apparatus according to claim 3 further comprising first color filters disposed in said first pair of slits and second color filters disposed in said second pair of slits, said first color filters passing rays having a wavelength different to that of the rays passing through said second color filter.

5. An apparatus according to claim 3 wherein said predetermined angle is substantially 20° to 30°.

6. An apparatus for detecting a defect on a pattern having a portion extending in a first direction and a portion extending in a second direction orthogonal to said first direction comprising:
    means for dark field illuminating said pattern with said first rays in said first direction and at a predetermined angle with respect to the surface of said pattern, and dark field illuminating said pattern with second rays in said second direction and at said predetermined angle with respect to said surface of said pattern, said illuminating means comprising a light source for irradiating rays, a slit plate having a first pair of slits and a second pair of slits through which the rays of said light source pass, and a condensing lens for directing the rays having passed through said first and second slits to said pattern at said predetermined angle so that the rays form said first and second rays, respectively, said first pair of slits being disposed in a single direction and symmetrically with respect to the center of said slit plate, said second pair of slits being disposed in a direction orthogonal to said last recited direction and symmetrically with respect to the center of said slit plate, said first pair of slits being so set as to be displaced clockwise by 45° from said first direction so that rays of said light source through said first pair of slits form said first rays, and said second pair of slits being so set as to be displaced clockwise 45° from said second direction so that the rays of said light source through said second pair of slits form said second rays; and
    means for detecting a first image signal of said pattern when said pattern is illuminated with said first rays and a second image signal of said pattern when said pattern is illuminated with said second rays, so that an image of a defect of said pattern is provided.

7. An apparatus according to claim 6, further comprising first color filters disposed in said first pair of slits and second color filters disposed in said second pair of slits, said first color filters passing rays having a wavelength different to that of the rays passing through said second color filter.

8. An apparatus for detecting a defect according to claim 7, wherein said first color filters pass rays of a blue color, and second color filters pass pays of a red color.

9. An apparatus for detecting a defect according to claim 6, wherein said predetermined angle is substantially 20° to 30°.

10. A method of detecting a defect on a pattern having a portion extending in a first direction and a portion extending in a second direction orthogonal to said first direction, comprising the steps of:
   dark field illuminating said pattern with first rays in said first direction and at a predetermined angle with respect to the surface of said pattern;
   detecting a first image signal of said pattern when said pattern is illuminated with said first rays;
   dark field illuminating said pattern with second rays in said second direction and at said predetermined angle with respect to said surface of said pattern;
   detecting a second image signal of said pattern when said pattern is illuminated with said second rays; and
   logically multiplying said first and second image signals to provide an image of a defect on said pattern.

11. A method according to claim 10, wherein said first and second rays have the same wavelength, and said steps are carried out in the order set forth.

12. A method according to claim 10, wherein said first rays have a first wavelength, said second rays have a second wavelength, said first and second recited dark field illuminating steps are carried out simultaneously, and said first and second detecting steps are carried out simultaneously.

13. A method according to claim 10, wherein said predetermined angle is substantially 20° to 30°.

14. A method of detecting a defect on a pattern having a portion extending in a first direction and a portion extending in a second direction orthogonal to said first direction, comprising the steps of:
   dark field illuminating said pattern with first rays in a direction displaced clockwise by 45° from said first direction and at a predetermined angle with respect to the surface of said pattern;
   detecting a first image signal of said pattern when said pattern is illuminated with said first rays;
   dark field illuminating said pattern with second rays in a direction displaced clockwise by 45° from said second direction and at a predetermined angle with respect to said surface of said pattern; and
   detecting a second image signal of said pattern when said pattern is illuminated with said second rays to provide an image of said defect.

15. A method according to claim 14, wherein said first and second rays have the same wavelength, and said steps are carried out in the order set forth.

16. A method according to claim 14, wherein said first rays have a first wavelength, said second rays have a second wavelength, said first and second recited dark field illuminating steps are carried out simultaneously, and said first and second recited detecting steps are carried out simultaneously.

17. A method of detecting a defect on a pattern according to claim 14, wherein said predetermined angle is substantially 20° to 30°.

* * * * *